United States Patent
Varner

(10) Patent No.: US 6,734,152 B1
(45) Date of Patent: May 11, 2004

(54) GLACIER SILT SOAP

(76) Inventor: Stephanie Lynn Varner, P.O. Box 35762, Juneau, AK (US) 99803

( * ) Notice: Subject to any disclaimer, the term of this patent is extended or adjusted under 35 U.S.C. 154(b) by 0 days.

(21) Appl. No.: 10/461,225

(22) Filed: Jun. 13, 2003

Related U.S. Application Data

(63) Continuation-in-part of application No. 10/218,319, filed on Aug. 13, 2002, now abandoned.

(51) Int. Cl.$^7$ .......................... C11D 13/16; C11D 13/02; C11D 9/04; C11D 3/14
(52) U.S. Cl. .................. 510/139; 510/130; 510/141; 510/146; 510/147; 510/152; 510/447; 510/440; 510/454
(58) Field of Search ................................ 510/130, 139, 510/141, 146, 147, 152, 440, 447, 454

(56) References Cited

U.S. PATENT DOCUMENTS 5,910,476 A * 6/1999 Kinsman et al. ............ 510/447
6,294,179 B1 * 9/2001 Lee et al. .................... 424/401

FOREIGN PATENT DOCUMENTS

EP          257458       * 3/1988

OTHER PUBLICATIONS

Copy of product description from Thunder Mountain Soaps.com.*

* cited by examiner

Primary Examiner—Charles Boyer
(74) Attorney, Agent, or Firm—Stephanie Lynn Varner

(57) ABSTRACT

A soap that contains glacier silt that is harvested in its natural form from areas previously occupied by glaciers. Glacial silt is one of the finest materials known. This silt is as fine or finer than talcum powder. The silt is heated to 400 degrees, sifted for a uniform consistency, and blended into cleaning compositions (soaps) used for human skin. Applied to human skin, the composition acts as mild pumice. Glacier silt is distinctive from other abrasives or pumices because the silt, in its natural form, is made up of very fine particles and is essentially undetectable when being used.

13 Claims, No Drawings

GLACIER SILT SOAP

CROSS REFERENCE TO RELATED APPLICATIONS

This application is a continuation-in-part of U.S. application Ser. No. 10/218319, filed Aug. 13, 2002, now abandoned.

STATEMENT REGARDING FEDERALLY SPONSORED RESEARCH AND DEVELOPMENT

Not Applicable

BACKGROUND OF THE INVENTION

1. Field of the invention

This invention relates to soap having silt incorporated therein and particularly to soap having glacial silt incorporated therein 2. Description of the Prior Art Soap has been used for centuries as a cleaning agent. Over the years, people have added various ingredients to soap to make it more pleasing and more efficient For example, fragrances are often added to soaps to provide a more pleasant smell. Years ago, pumice was added to soap to make it work better. It is believed that the pumice provided grit that helped scrub grease and other substances from the skin.

There are two basic methods of making soap. The first is the cold process. This process is a soap making method where no additional heat is added during the process. The chemical heat from the saponification process (gel stage) is the only heat in this method causing saponification to take place during its curing time, which is the time that process soap is allowed to sit before using, usually 4 weeks. This time allows cold process soap to slowly saponify and become less harsh In addition, it allows the water to evaporate out creating a harder bar.

The second method is known as the hot process. The hot process is a process in which additional heat is added during the soap making process. The soap is heated up either in a microwave oven or crock-pot (for small batches) to create soap quickly. The additional heat helps the soap go through the saponification process much faster than the 4 weeks that cold process soap is allowed to cure. The additional heat helps the soap to form. It also removes much of the excess water so that soap made this way is ready to use as soon as it has cooled.

BRIEF DESCRIPTION OF THE INVENTION

The instant invention is a soap that contains glacier silt that is harvested in its natural form from areas previously occupied by glaciers. Glacial silt is one of the finest materials known. This silt is as fine or finer than talcum powder. The silt is heated to 400 degrees, sifted for a uniform consistency, and blended into cleaning compositions (soaps) used for human skin. Applied to human skin, the composition acts as mild pumice. Glacier silt is distinctive from other abrasives or pumices because the silt, in its. natural form, is made up of very fine particles and is essentially undetectable when being used.

My process uses the hot process for making soap. Once the silt has been cleaned dried and heated, it is mixed into the soap during the process. Because the hot process is used, the soap cures quickly. It is important to keep mixing the soap as it cures to ensure that the silt is evenly spread through the soap when it has cured.

DETAILED DESCRIPTION OF THE INVENTION

Silt Soap Process

First, the silt is gathered and prepared.

As noted above, the silt used in this process comes from glacial remains. The silt selected is silt wet and "slick" to the touch (no gritty feel).

The wet silt is gathered and air-dried. Depending on the density of the silt and the wetness, the drying time varies from two weeks to two months. The silt is considered ready to use when it reaches a level of dryness determined by feel. The silt is dry enough if it clings to a finger when touched, or blows away when blown upon.

The silt is further treated by heating for several (at least 6) hours at 400 degrees. During the heating, the silt is turned several times. The heating is done to kill water organisms and possibly burn off anything like grass or other foreign materials that may be contained in the silt. After the heating process, the silt is allowed to cool.

Next, the silt is sifted to ensure that only the finest, debris-free silt is used in the soap. After sifting, the silt has the consistency of powdered sugar.

To make the soap, the following process is used:

Blocks of clear glycerin-based soap are cut into chunks approximately 3 inches long, by 2 inches wide, by ½ inch thick. These chunks are heated in warming pots at 225 degrees until melted. Fragrance and color are added to this clear melted base, which is then poured into 20 section 8.5 lb tray molds, or whatever size molds are desired.

Concurrent to the above process steps, blocks of white glycerin-based soap are cut and melted in warming pots at between 195 and 200 degrees. Once the white soap is melted into a liquid, the fine silt powder is added. Because the silt tends to be encapsulated by the soap and floats, a whisk, or similar mixing instrument must be used to distribute the silt throughout the liquid evenly. This takes a bit of finesse because if the silt is not encapsulated and floating, it tends to sink to the bottom. Thus, it must be kept moving until the mixture cools sufficiently to hold the silt in place. This is accomplished by continuously stirring the mixture until it cools Thus, it is important to keep the stirring process even, so that the silt is spread throughout the mixture evenly. The silt/soap mixture must be stirred until it cools to 100.1 degrees Fahrenheit. This is precisely the temperature at which the silt/soap mixture begins turning from a liquid to a solid, but before it actually gels. At this temperature, the silt is perfectly suspended in the liquid.

The clear soap base (which is still cooling) has developed, by this time, a slight film on top. Rubbing alcohol (70% Isopropyl and deionized water) is then misted onto this film surface. This acts as a bonding agent.

After the alcohol mist, the white silt/soap mixture is added to the clear soap. This is the artistic part of the process. This step produces an aesthetic blend of clear and white soap in a number of different patterns by swirling the mixture as the white silt/soap is added to the clear soap.

The above steps are repeated and a second layer is added to the molds and the entire mixture is allowed to cool.

After the soap is solid, it released from the molds and cut into bars.

The pre-made soap base is commercially available and the ingredients for this base typically are as follows: coconut oil, palm oil, castor oil, safflower oil, glycerin (of vegetable origin), purified water, sorbitol (moisturizer), sorbitan oleate (emulsifier), soy bean protein (conditioner), EDTA (water softener).

The white soap base is also commercially available. It has the same ingredients as the clear soap base with addition of Titanium Dioxide.

The present disclosure should not be construed in any limited sense other than that limited by the scope of the claims having regard to the teachings herein and the prior art being apparent with the preferred form of the invention disclosed herein and which reveals details of structure of a preferred form necessary for a better understanding of the invention and may be subject to change by skilled persons within the scope of the invention without departing from the concept thereof.

I claim:

1. A method of making soap comprising the steps of:
   a) heating blocks of clear glycerin-based soap until said blocks are melted;
   b) pouring said melted blocks of clear glycerin-based soap into a quantity of tray molds;
   c) heating bocks of white glycerin-based soap until said blocks are melted;
   d) adding a quantity of glacial silt to the melted blocks of white glycerin-based soap;
   e) stirring said melted blocks of white glycerin-based soap until said quantity of glacial silt is mixed into said melted blocks of white glycerin-based soap and said melted blocks of white glycerin-based soap begin to harden;
   f) mixing the white glycerin-based soap and glacial mixture into said melted blocks of clear glycerin-based soap; and
   g) allowing the mixture of the white glycerin-based soap and glacial mixture into said melted blocks of clear glycerin-based soap to harden.

2. The method of claim 1 wherein the clear glycerin-based soap is heated in a warming pot at 225 degrees F.

3. The method of claim 1 further comprising the steps of:
   a) adding a quantity of fragrance to the clear glycerin-based soap; and
   b) adding a quantity of color to the clear glycerin-based soap.

4. The method of claim 1 wherein the white glycerin-based is heated in a warming pot at between 195 and 200 degrees F.

5. The method of claim 1 wherein in step e, the mixture of white glycerin-based soap and glacial silt is stirred until it cools to 100.1 degrees Fahrenheit.

6. The method of claim 1 further comprising the step of:
   a) prior to step f, misting a quantity of rubbing alcohol onto the melted clear glycerin-based soap.

7. The method of claim 1 further comprising the steps of:
   a) after step f, repeating steps a–f with a new quantity of clear glycerin-based soap, white glycerin-based soap, and glacial silt;
   b) adding the second mixture to the tray molds; and
   c) allowing the entire mixture to cool forming a cooled mixture.

8. The method of claim 1 further comprising the steps of:
   a) collecting a quantity of wet glacial silt;
   b) allowing said quantity of wet glacial silt to air dry;
   c) heating said quantity of dried silt for a quantity of time;
   d) allowing the heated quantity of glacial silt to cool; and
   e) sifting said quantity of glacial silt.

9. the method of claim 8 wherein the quantity of wet glacial silt is air dried for between about two and eight weeks.

10. The method of claim 8 wherein the quantity of air-dried glacial silt is heated to about 400 degrees F.

11. The method of claim 8 wherein the quantity of air-dried glacial silt is heated for six hours.

12. The method of claim 8 wherein the step of heating the quantity of dried silt for a quantity of time further comprises the step of turning the quantity of dried silt at least once.

13. The method of claim 8 wherein the step of heating the quantity of dried silt for a quantity of time further comprises the step of turning the quantity of dried silt a plurality of times.

* * * * *